(12) United States Patent
Kondis et al.

(10) Patent No.: US 11,484,200 B2
(45) Date of Patent: Nov. 1, 2022

(54) LIGHT-ADJUSTABLE LENS ILLUMINATION SYSTEM WITH FOVEA PROTECTION

(71) Applicant: RxSight, Inc., Aliso Viejo, CA (US)

(72) Inventors: John Kondis, Irvine, CA (US); Robert Maloney, Los Angeles, CA (US); Ilya Goldshleger, Ladera Ranch, CA (US); Matt Haller, Costa Mesa, CA (US); Christian A. Sandstedt, Pasadena, CA (US)

(73) Assignee: RxSight, Inc., Aliso Viejo, CA (US)

( * ) Notice: Subject to any disclaimer, the term of this patent is extended or adjusted under 35 U.S.C. 154(b) by 460 days.

(21) Appl. No.: 16/354,128

(22) Filed: Mar. 14, 2019

(65) Prior Publication Data

US 2020/0292834 A1 Sep. 17, 2020

(51) Int. Cl.
| | | |
|---|---|---|
| A61F 2/16 | (2006.01) | |
| A61F 9/00 | (2006.01) | |
| A61F 9/008 | (2006.01) | |
| A61B 18/20 | (2006.01) | |
| A61B 3/125 | (2006.01) | |

(52) U.S. Cl.
CPC .............. *A61B 3/125* (2013.01); *A61B 18/20* (2013.01); *A61F 2/16* (2013.01); *A61F 9/008* (2013.01); *A61F 9/0017* (2013.01); *A61B 2018/20351* (2017.05); *A61F 2002/1699* (2015.04); *A61F 2009/0087* (2013.01); *A61F 2009/00863* (2013.01); *A61F 2240/008* (2013.01)

(58) Field of Classification Search
CPC .................. A61B 3/125; A61B 18/20; A61B 2018/20351; A61F 9/008; A61F 9/0017; A61F 2/16; A61F 2009/0087; A61F 2240/008; A61F 2009/00863; A61F 2002/1699; A61F 2/1624; A61F 2002/1696
See application file for complete search history.

(56) References Cited

U.S. PATENT DOCUMENTS

| | | | |
|---|---|---|---|
| 6,905,641 B2 | 6/2005 | Platt et al. | |
| 2002/0100990 A1* | 8/2002 | Platt ........................ | A61F 9/008 264/1.38 |
| 2011/0202114 A1* | 8/2011 | Kessel .................... | A61F 9/008 607/88 |
| 2012/0310141 A1* | 12/2012 | Kornfield ................ | A61P 27/02 604/20 |
| 2016/0236006 A1* | 8/2016 | Donitzky .............. | A61F 9/0079 |

* cited by examiner

*Primary Examiner* — Brian T Gedeon
*Assistant Examiner* — Joshua Andrew Schum-Houck
(74) *Attorney, Agent, or Firm* — Gergely T. Zimanyi (57) ABSTRACT

A light adjustable lens illumination system comprises an illumination source, for generating a light beam; a light delivery system, for projecting the light beam onto a Light Adjustable Lens (LAL), implanted into an eye, wherein a fraction of the light beam propagates past the LAL to a retina of the eye; and a protective beam-shaper, for shaping the light beam to have an intensity pattern with a relative central intensity reduction that varies along an axis; wherein the relative central intensity reduction at the retina is greater than the relative central intensity reduction at a LAL plane.

14 Claims, 11 Drawing Sheets

FIG. 5A protective intensity pattern 201p

LIGHT-ADJUSTABLE LENS ILLUMINATION SYSTEM WITH FOVEA PROTECTION

TECHNICAL FIELD

This patent document describes illumination systems for light adjustable lenses, and in more detail, illumination systems with fovea protection.

BACKGROUND

The techniques of cataract surgery are progressing at an impressive pace. Generations of phacoemulsification platforms and more recently introduced surgical lasers keep increasing the precision of the placement of intraocular lenses (IOLs) and keep reducing unintended medical outcomes. Nevertheless, after the IOLs have been implanted, the postsurgical healing process can shift or tilt the IOLs in a notable fraction of the patients, leading to a diminished visual acuity, and a deviation from the planned surgical outcome.

A new technique has been developed recently to correct or mitigate such a postsurgical IOL shift or tilt. The new technique is capable of adjusting the optical properties of the IOLs with a postsurgical procedure to compensate the shift or tilt of the IOL. As described in commonly owned U.S. Pat. No. 6,905,641, to Platt et al, entitled: "Delivery system for post-operative power adjustment of adjustable lens", hereby incorporated by reference in its entirety, the IOLs can be fabricated from a photo-polymerizable material, henceforth making them Light Adjustable Lenses, or LALs. In the days after the surgery, the implanted LALs may shift and tilt, eventually settling into a postsurgical position different from what the surgeon planned. Once the LAL settled, a Light Delivery Device (LDD) can be used to illuminate the LALs with a UV light having an illumination pattern that induces photopolymerization of the macromers in the LAL with a corresponding spatial pattern, thus changing the refractive optical properties of the LALs. This refractive change adjusts the LAL optical performance to compensate the unintended postsurgical shift or tilt of the LAL. Once the optical characteristics of the implanted LAL is achieved by the light-induced photopolymerization, a final "lock-in" illumination can be applied to photopolymerize the remaining macromers in a manner that does not further change the optical properties of the LAL. The LAL technology enables the physician to adjust the optical characteristic of the implanted LAL post-surgically and non-invasively, and thus promises to greatly improve the medical outcome of cataract surgery and thus patient satisfaction.

While present day LDDs are safe, it is still prudent to further enhance the safety of this promising LAL technology. One of the motivations is that the illumination is performed with a UV light, for which the human retina is particularly sensitive. The part of the retina with the highest UV-light sensitivity is the fovea, a small central region where most of the color-sensing cones are located. Therefore, there is a need for Light Delivery Devices that provide additional protection for the fovea.

SUMMARY

Embodiments address the above medical needs as follows. Some embodiments of a light adjustable lens illumination system comprise an illumination source, for generating a light beam; a light delivery system, for projecting the light beam onto a Light Adjustable Lens (LAL), implanted into an eye, wherein a fraction of the light beam propagates past the LAL to a retina of the eye; and a protective beam-shaper, for shaping the light beam to have an intensity pattern with a relative central intensity reduction that varies along an axis; wherein the relative central intensity reduction at the retina is greater than the relative central intensity reduction at a LAL plane.

DETAILED DESCRIPTION

Figure 1:
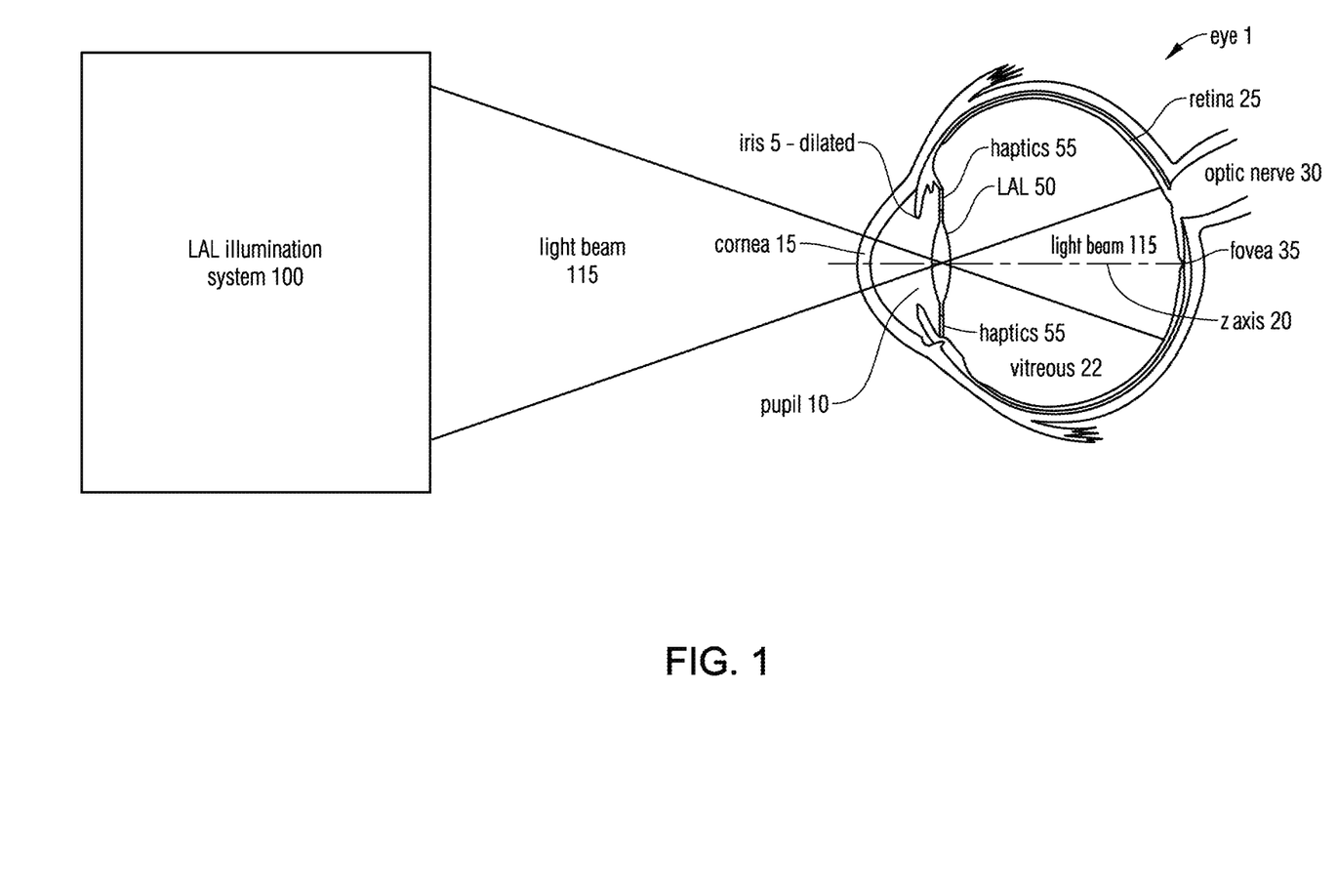
FIG. 1 illustrates a Light Adjustable Lens (LAL) illumination system.
Figure 2:
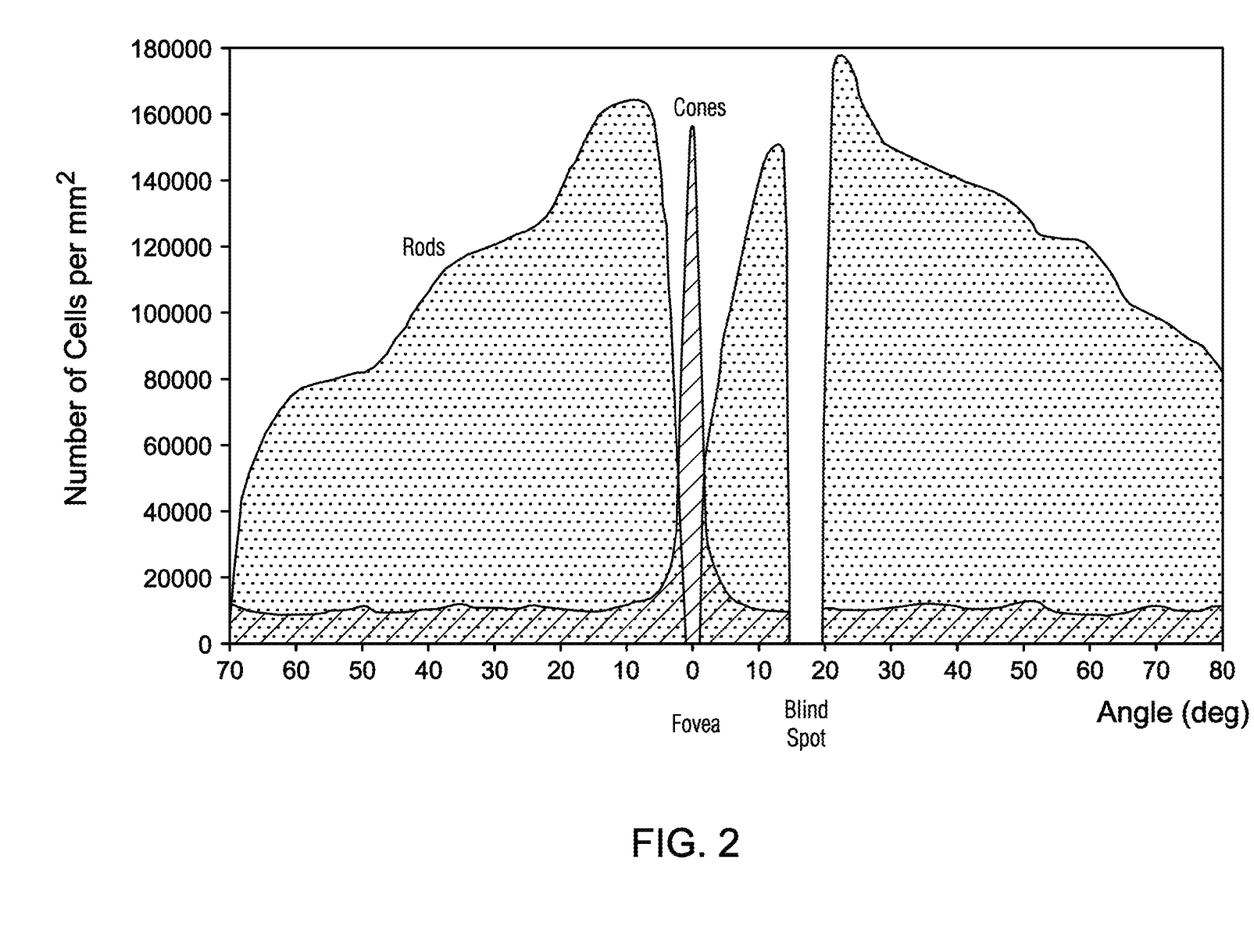
FIG. 2 illustrates the density of cones on the retina.
Figure 3A:
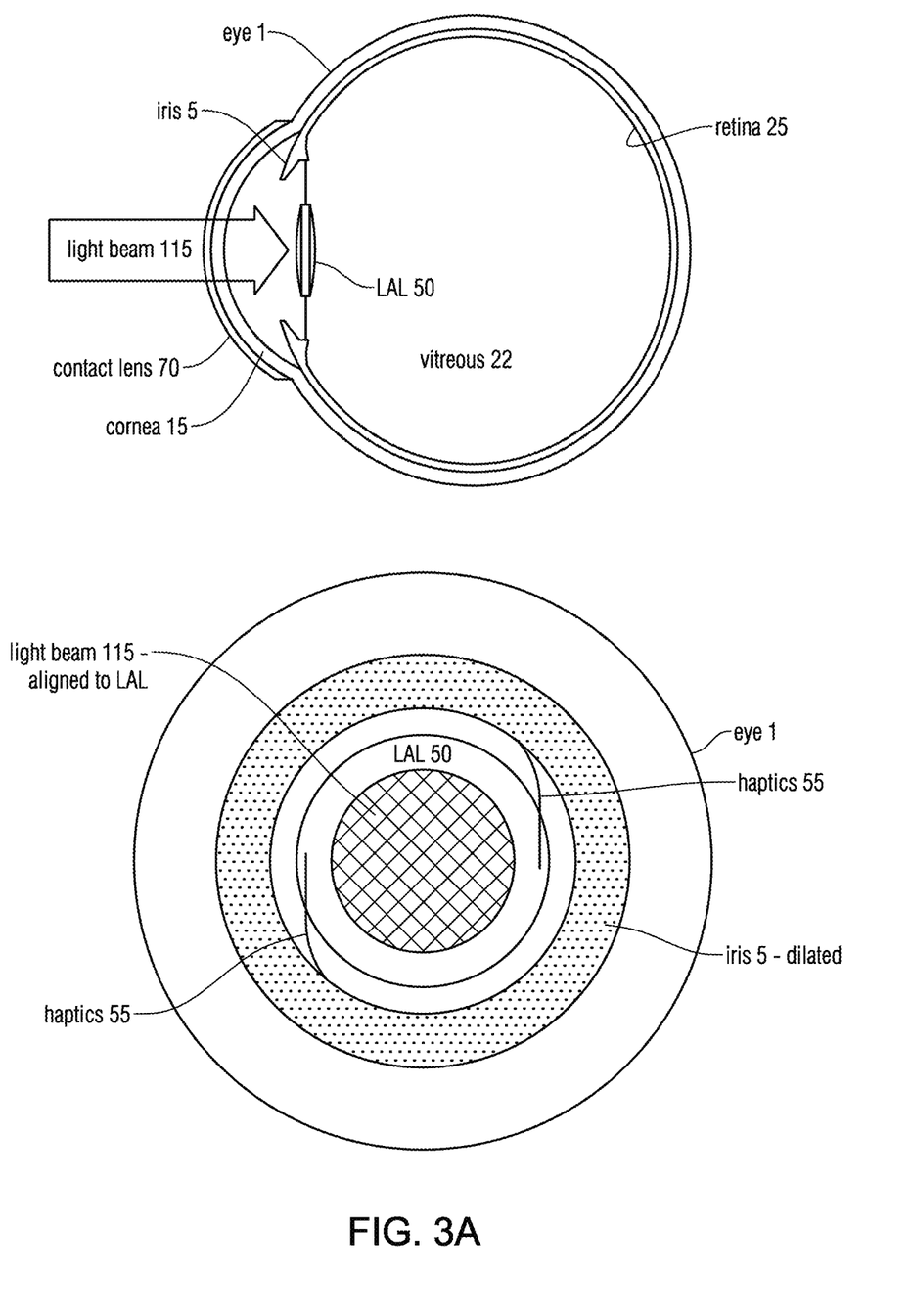
FIGS. 3A-B illustrate a problem of misalignment of an illuminating light beam.
Figure 3B:
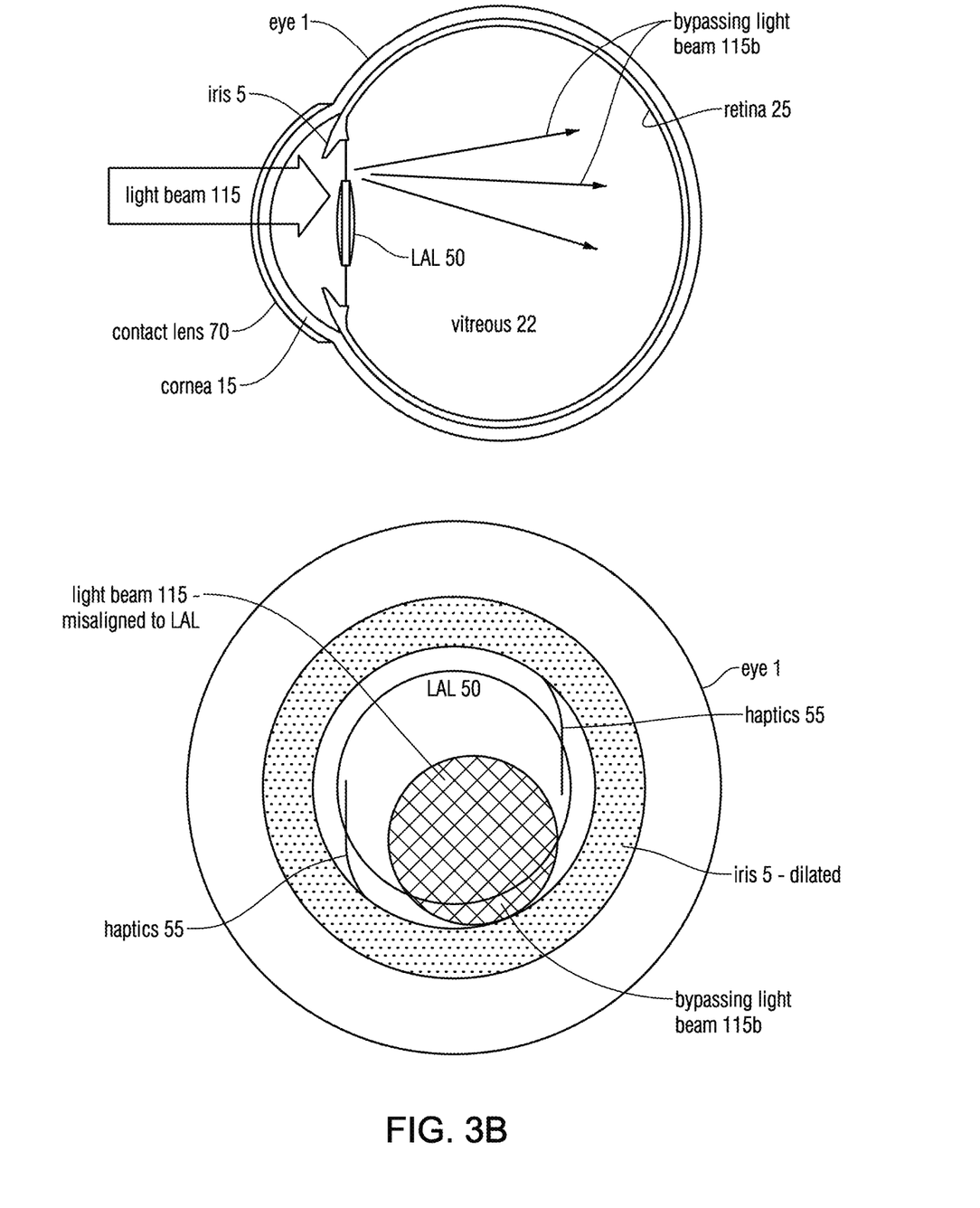

FIGS. 1-3 illustrate the previously discussed medical need in some detail. FIGS. 4-8 illustrate embodiments that provide solutions for this medical need.

FIG. 1 shows a Light Adjustable Lens (LAL) illumination system 100 that generates a light beam 115 and propagates, or delivers, the light beam 115 into an eye 1. The eye 1 includes an annular iris 5 that defines a central opening, a pupil 10. The iris 5 is typically dilated for the illumination procedure, as indicated. The incoming light beam 115 enters the eye through a cornea 15 and propagates through the pupil 10 along an axis 20. The light beam 115 propagates through a vitreous 22 and eventually reaches a retina 25 at a posterior end of the eye 1. Two features of this posterior end are mentioned here expressly and illustrated in FIG. 2. First, an optical nerve 30 collects and transmits the visual stimuli from the retina 25 and transmits them towards the brain. The spot where the optic nerve 30 leaves the eye 1 has practically no light-sensing cells, known as rods and cones, and is hence often called a blind spot. The other feature of note is a fovea 35, where a density of color-sensing cones has a sharp, narrow peak. These cones are particularly sensitive to light. FIG. 2 illustrates how sharply localized this peak is: a typical fovea 35 has a radius of about 1.5 mm.

The light beam 115 is directed by the LAL illumination system 100 at a LAL 50, implanted in the eye 1 and stabilized in place by haptics 55 in a capsular bag, from which the natural cataractous crystalline lens of the eye has been removed. For some classes of LALs, this illumination light can be a UV light beam with sufficient intensity to adjust the optical properties of the LAL 50 by photopolymerization. There are various ways to protect the retina 25 from the undesirable effects of this intense UV light. First, the composition of the LAL 50 includes light-absorbing components, such as dispersed UV absorber molecules. Second, a UV-blocking back-layer can be also formed at a posterior surface of the LAL 50. The UV absorbers dispersed in the volume of the LAL 50, and disposed in its back-layer greatly reduce the intensity of the illumination light as it propagates across the LAL 50, so that only a very small portion of the incident light beam 115 manages to get through the LAL 50 and continue to propagate across the vitreous 22 to the retina 25. Some LALs allow less than 1% of the incoming UV light to pass through. Others allow less than 0.1% of the light to pass through. Nevertheless, it is prudent to further enhance the retinal safety by implementing additional protections, especially for the retina's most sensitive area, the fovea 35.

FIGS. 3A-B illustrate a second motivation to enhance the protection of the retina 25 and especially the fovea 35. When the illumination beam 115 is directed into the eye 1, the light beam 115 needs to be aligned with the LAL 50. Here the term aligned is short for aligning the axis 20 of the light beam 115 with an optical axis of the LAL 50, and centering the light beam 115 to the center of the LAL 50. The physician, or ophthalmologist who performs the procedure, is sometimes advised to place a contact lens 70 onto the cornea 15, and manually manipulate the contact lens 70, and thus the eye 1, so that the light beam 115 is aligned with the LAL 50. In spite of the best intentions of the physician, the effort to align the light beam 115 and the LAL 50, and to keep them aligned, may not be fully successful. An involuntary eye movement, a head movement, a sneezing, an alarmed patient reaction can all cause such misalignment, at least for a short time. FIG. 3B shows that in such cases, the light beam 115 can bypass the LAL 50 at least in a small region, as a bypassing light beam 115b. For these short and fractional misalignments, the volumetric and back-layer UV absorbers of the LAL 50 will not reduce the intensity of the bypassing light beam 115b. The UV bypassing light beam 115b impacting the retina 25 in general and its most sensitive region, the fovea 35, in particular, can lead to undesirable medical outcomes. This is a second reason to develop and implement additional protective technologies in the LAL illumination system 100.

Figure 4:
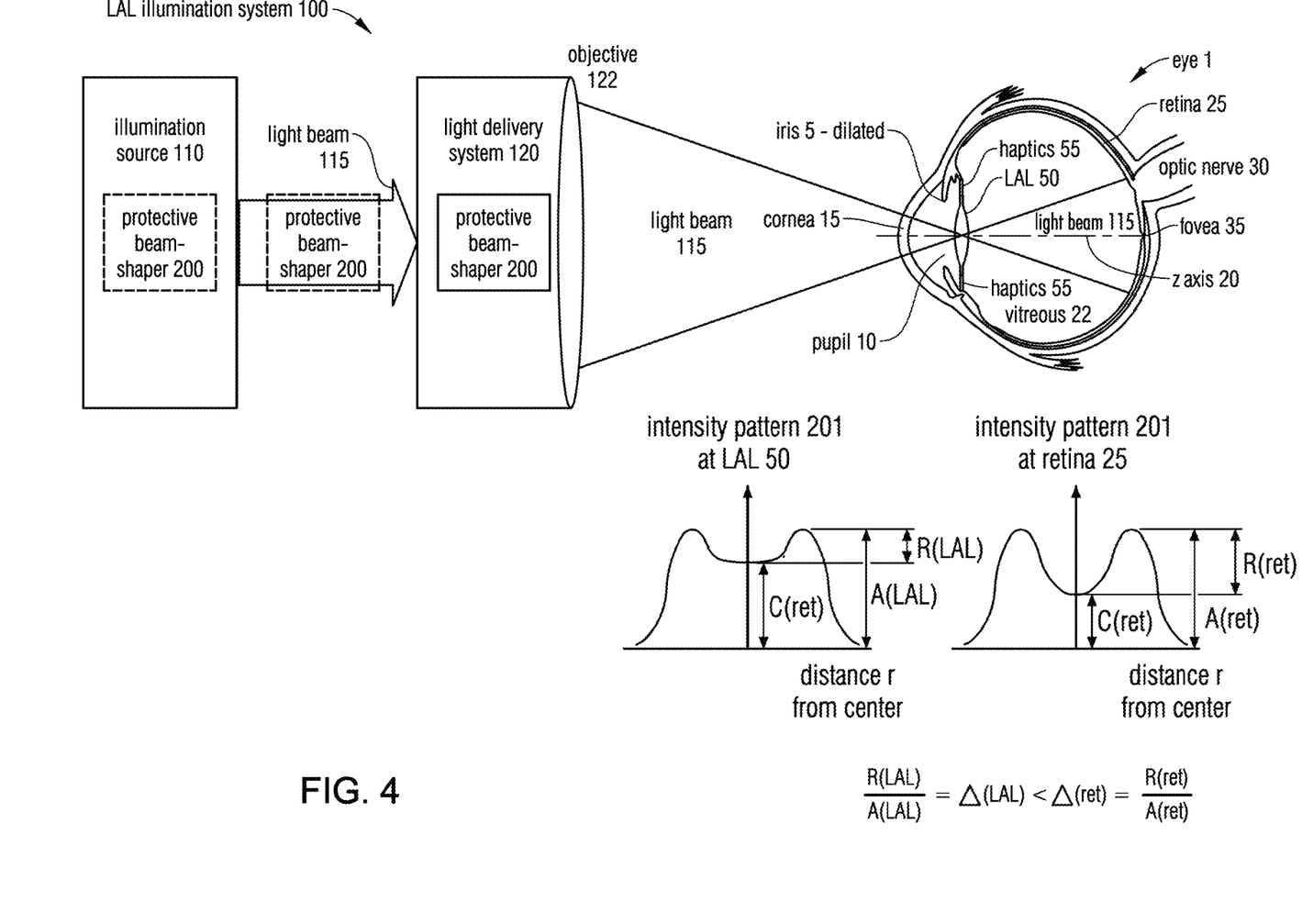
FIG. 4 illustrates a Light Adjustable Lens (LAL) illumination system with a protective beam shaper.

FIG. 4 illustrates a LAL illumination system 100 that includes such protective technologies. The LAL illumination system 100 can include an illumination source 110, for generating the light beam 115; a light delivery system 120, for projecting the light beam 115 onto a Light Adjustable Lens (LAL) 50, implanted into an eye 1, so that a fraction of the light beam 115 propagates past the LAL 50 to a retina 25 of the eye 1; and a protective beam-shaper 200, for shaping the light beam 115 to have an intensity pattern 201 with a relative central intensity reduction that varies along an axis 20; wherein the relative central intensity reduction at the retina 25 is greater than the relative central intensity reduction at a LAL plane.

This beam-shaping is innovative, as it simultaneously satisfies competing and seemingly contradictory requirements. The protective beam-shaper 200 is designed to greatly reduce a central intensity of the light beam 115 at the retina 25 to protect the fovea 35, while reducing the central intensity of the light beam 115 only moderately at the LAL plane, so that the optical characteristics of the LAL 50 are not modified by the shaped intensity pattern of the light beam 115.

The protective beam shaper 200 can be part of the light delivery system 120, as shown. In other embodiments, it can be a self-standing block, or part of the illumination source 110, as indicated by the dashed line.

Examples of the discussed intensity patterns are illustrated in the right panel of FIG. 4. The intensity of the light beam 115 can have the following radially varying intensity pattern 201 at a specific axial coordinate z. Approaching from outer distances r from the center, the intensity is rising with decreasing distance r, as it is typical for ordinary beams, like Gaussian beams. The intensity pattern 201, however, reaches a maximum A, and with further decreasing r, the intensity starts dropping towards a reduced beam center intensity C, at r=0, by a reduction R=A−C. This dependence of the intensity pattern 201 of the radial distance r is shown in the lower right panel of FIG. 4. The arguments of A(z), C(z) and R(z) indicate the axial (z) coordinate along the axis 20 of the intensity pattern 201: A(LAL), C(LAL) and R(LAL) denote the maximum A, the reduced beam center intensity C, and the reduction R at the z axial coordinate where a plane of the LAL 50 intersects the axis 20, whereas A(ret), C(ret) and R(ret) denote the same at the retina.

With this preparation, the described relative central intensity reduction of the intensity pattern 201, denoted by $\Delta$, can be thought of as a ratio of the maximum intensity A minus the reduced beam center intensity C, i.e. A−C=R, divided by the maximum intensity A: $\Delta=(A-C)/A=R/A$. With this definition, the protective beam-shaper 200 shaping the light beam 115 to have the above intensity patterns 201 at the LAL plane and at the retina can be captured in Eq. (1) as follows:

$$\frac{R(LAL)}{A(LAL)} = \Delta(LAL) < \Delta(ret) = \frac{R(ret)}{A(ret)} \qquad (1)$$

Figure 5A:
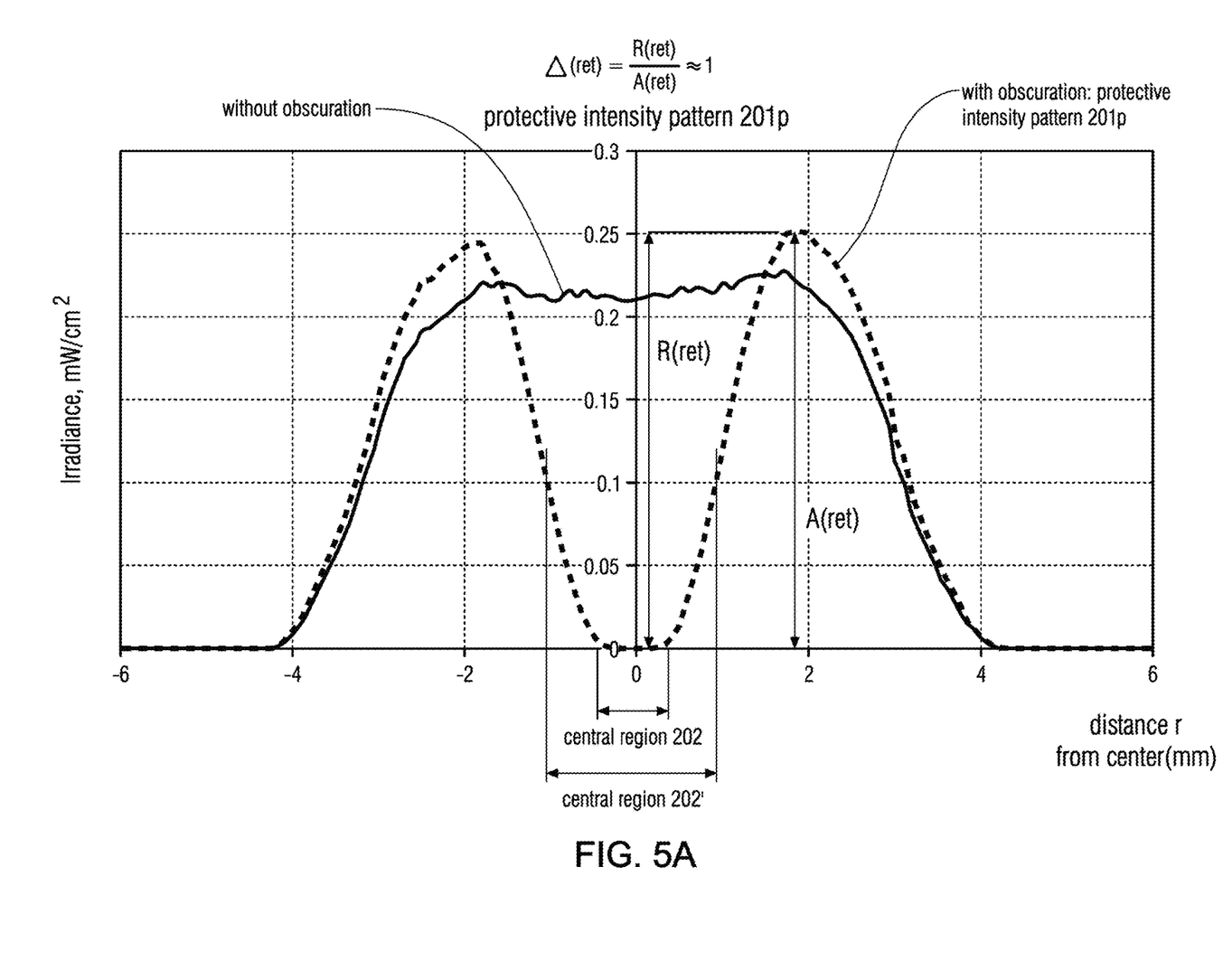
FIGS. 5A-C illustrate various intensity patterns, including protective intensity patterns.

FIG. 5A illustrates that the reduction of the beam center intensity can have an extended minimum, such as a flat minimum over a central region 202, where an irradiance of the intensity pattern is approximately flat. The protective beam-shaper 200 can be configured to shape the light beam 115 so that this central region 202 of the illumination pattern 201 at the retina 25 is positioned to include the fovea 35 of the eye 1. With such a beam-shaping, the protective beam-shaper 200 can provide a solution for the medical need of the LAL illumination system 100, described in the opening remarks: to protect the fovea 35 by substantially reducing the intensity of the light beam 115 that impacts the fovea 35.

FIG. 5A shows, a typical intensity pattern 201 as shaped by the protective beam-shaper 200. The intensity can be measured, e.g., in terms of an irradiance, with units of power over area, in the present case, $mW/cm^2$. The intensity pattern 201 of the light beam 115 at the retina 25 can be called a protective intensity pattern 201p, if the reduced beam center intensity C(ret) in the central region 202 is less than a threshold to fully protect the fovea 35. In some embodiments, this protection threshold is the reduced beam center intensity C(ret) being less than 0.1 $mW/cm^2$. In other embodiments, the protective intensity pattern 201p can have a reduced beam center intensity C(ret) less than 1 $mW/cm^2$, in yet others, less than 0.01 $mW/cm^2$. For comparison, the intensity pattern 201 is also shown when the protective beam-shaper 200 is removed from the LAL illumination system 100. Visibly, this intensity pattern 201 has no reduction at the center, and thus is not a protective intensity pattern 201p.

To place these irradiance values in the context of the light adjustable lens technology, the illumination source 110 typically generates a light beam 115 with a wavelength in a range of 300 nm-450 nm, often in the range of 350 nm-400 nm, making the light beam 115 a UV beam. This UV light beam 115 is directed onto the LAL 50 to photopolymerize macromers in a spatial adjustment pattern corresponding to the adjustment intensity pattern of the light beam 115, which is formed to adjust the optical properties of the LAL 50. In typical cases, once the desired adjustment of the optical properties has been achieved, the LAL 50 still contains remaining photopolymerizable macromers in a certain concentration. Subsequent uncontrolled, or uneven photopolymerization of these remaining macromers could change the refractive properties of the LAL 50 away from the values intended by the physician. To prevent such undesirable developments, all remaining photopolymerizable macromers are neutralized in a subsequent lock-in process. In this lock-in process, the illumination source 110 applies a lock-in light beam 115 to the LAL 50 to photopolymerize all remaining macromers in a manner that does not further adjust the optical properties of the LAL 50. This step thus "locks in" the previous light adjustment of the LAL 50. To make sure that essentially no photopolymerizable macromers are left behind that could alter the previously induced optical adjustment, the intensity of the light beam 115 of the lock-in illumination is chosen to be sufficiently high. Light beam intensities during the lock-in illumination can reach 100-1,000 mW/cm$^2$, in others 200-400 mW/cm$^2$, with corresponding energy densities of 10-100 J/cm$^2$, in others, 20-40 J/cm$^2$. The correspondence is further impacted by the procedure time, which can be 10-150 sec, in some cases 60-100 sec. All quantities are referenced at the plane of the LAL 50. Moreover, the lock-in illumination in some cases can have a radial pattern, where a peak-to-edge ratio can be in the range of 1.5-10, in other cases 2-5. Therefore, the protection of the fovea 35 is the most pressing during the lock-in illumination. In some embodiments of the LAL illumination system 100, the protective beam-shaper 200 can create a protective intensity pattern 201$p$ with a central intensity C(ret) less than the above recited limits of 1 mW/cm$^2$, 0.1 mW/cm$^2$, or 0.01 mW/cm$^2$, even during a lock-in illumination that have the just described high intensities.

FIG. 5A shows that the definition of the central region 202 may involve some ambiguity. For an intensity pattern 201 with a flat region in the center, the flat region may be called the central region 202. For round intensity patterns without a flat region in the center, the diameter of central region 202' can be defined where the irradiance got reduced to 50% of its value at its maximum at A, as shown. Other, analogous definitions of the central region 202 can be also adopted, for example, with reduction to 30%, or 20%, of the maximum. With this context, in some embodiments, a diameter of the central region 202 can be less than 2.5 mm, 2 mm, or 1.5 mm. Here it is recalled that a typical diameter of the fovea 35 is about 1.5 mm, thus the above listed diameters of the central region 202 are suitable to provide full foveal protection.

Figure 5B:
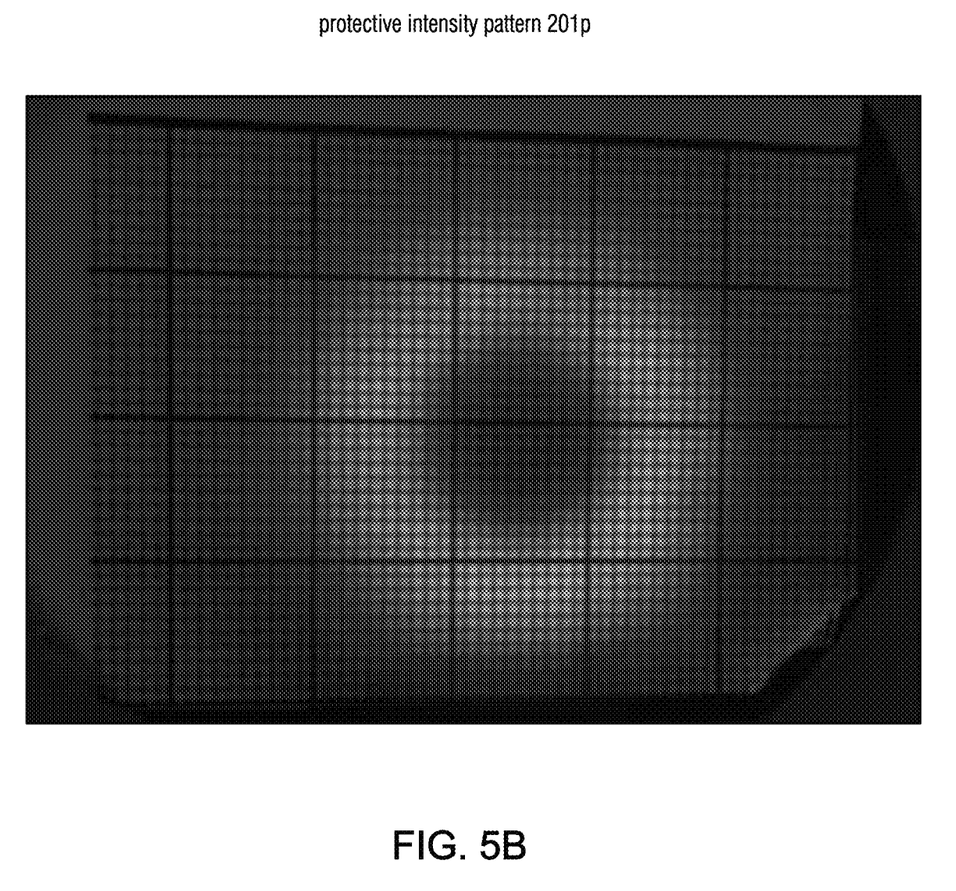

FIG. 5B shows the protective intensity pattern 201$p$ of FIG. 5A as a heat map, over a retinal plane. Lighter colors indicate higher irradiance. In the graphs of FIGS. 5A-B, visibly the intensity reduction is essentially complete, and thus C(ret) is approximately zero, R(ret) is approximately equal to A(ret), and therefore the relative central intensity reduction of this protective intensity pattern 201$p$, Δ(ret), is approximately 1.

Figure 5C:
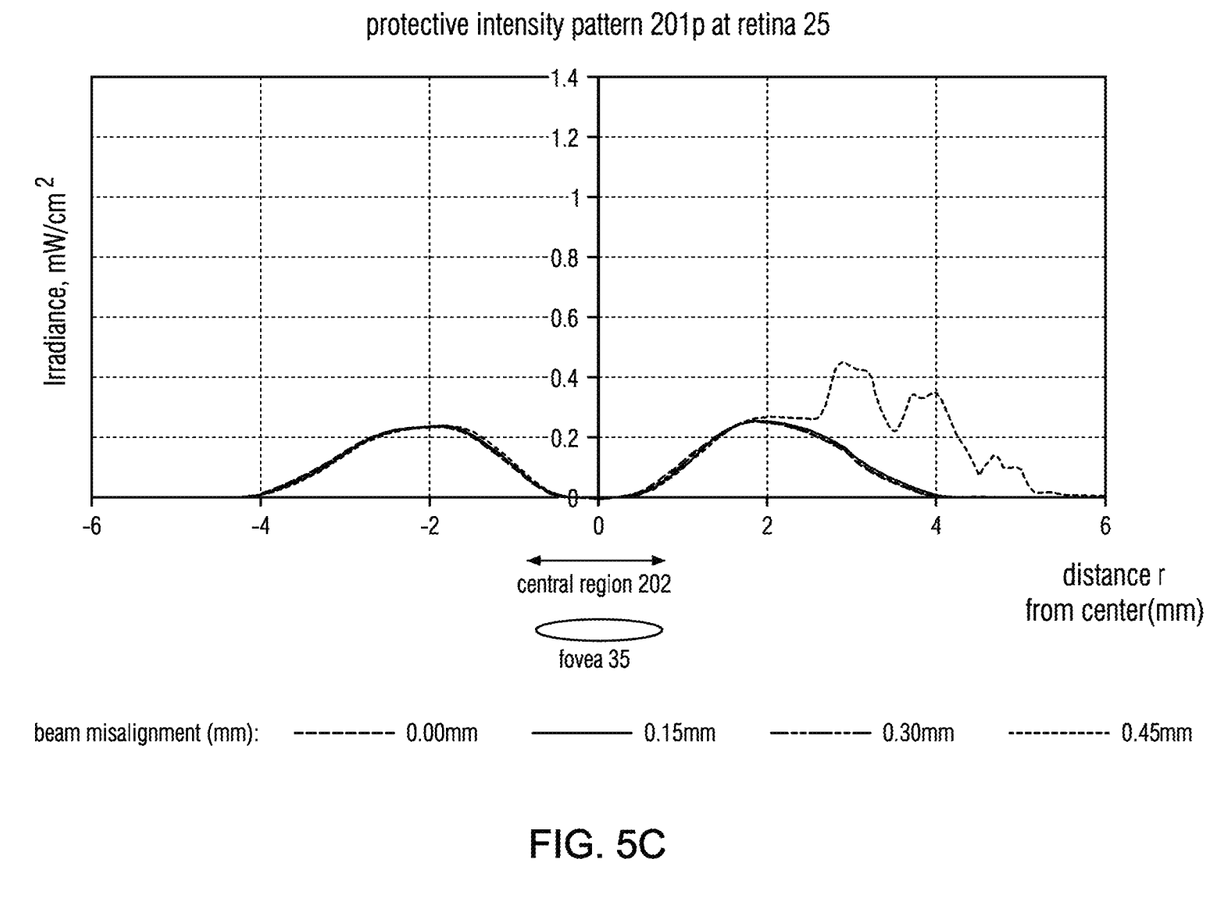

FIG. 5C illustrates that the protective beam shaper 200 can shape the light beam 115 to offer a solution for the other medical need described earlier: the mitigation of the retinal impact of a potentially bypassing light beam 115$b$ in case of a misalignment between the light beam 115 and the LAL 50. Four curves show the irradiance of the protective intensity pattern 201$p$ for light beams whose axis 20 is misaligned from a center of the LAL 50 by 0 mm (aligned), 0.15 mm, 0.30 mm, and 0.45 mm. Visibly, for the first three misalignment values of 0-0.30 mm, C(ret) remains essentially zero, and thus the fovea 35 remains fully protected. Even for the largest misalignment of 0.45 mm, while a small fraction of the misaligned bypassing light beam 115$b$ reaches the retina 25, it does so only far away from the fovea 35. The reduction R(ret) of the intensity pattern at the fovea 35 (at the center) remains essentially complete, and the relative central intensity reduction of the protective intensity pattern 201$p$, Δ(ret), remains approximately 1.

The relative central intensity reduction at the retina, Δ(ret), can be greater than the relative central intensity reduction at the LAL, Δ(LAL), in different manners. In some embodiments, the relative central intensity reduction at the retina, Δ(ret), can be greater than 30%, while the relative central intensity reduction at the LAL plane, Δ(LAL), can be less than 30%. In other embodiments, the relative central intensity reduction at the retina, Δ(ret), can be greater than 50%, while the relative central intensity reduction at the LAL plane, Δ(LAL), can be less than 20%.

Figure 6:
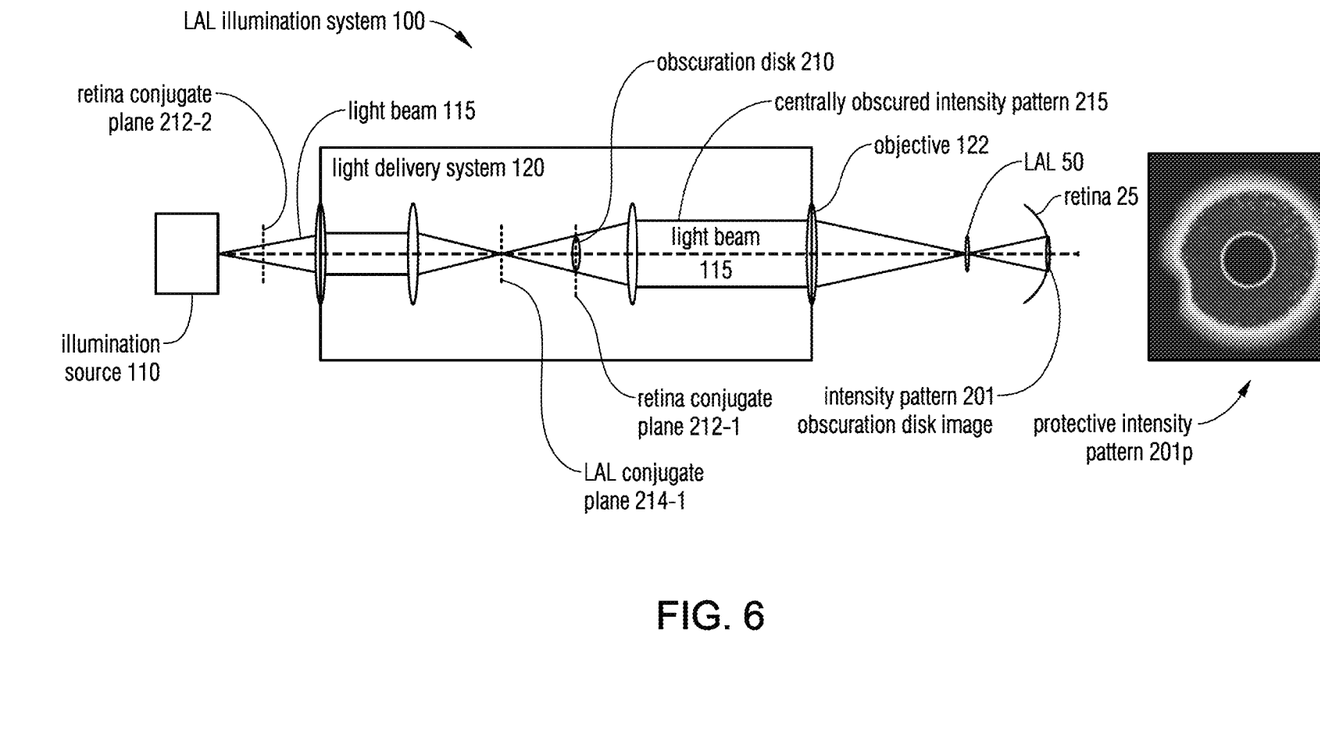
FIG. 6 illustrates an obscuration disk embodiment of the protective beam shaper.
Figure 7:
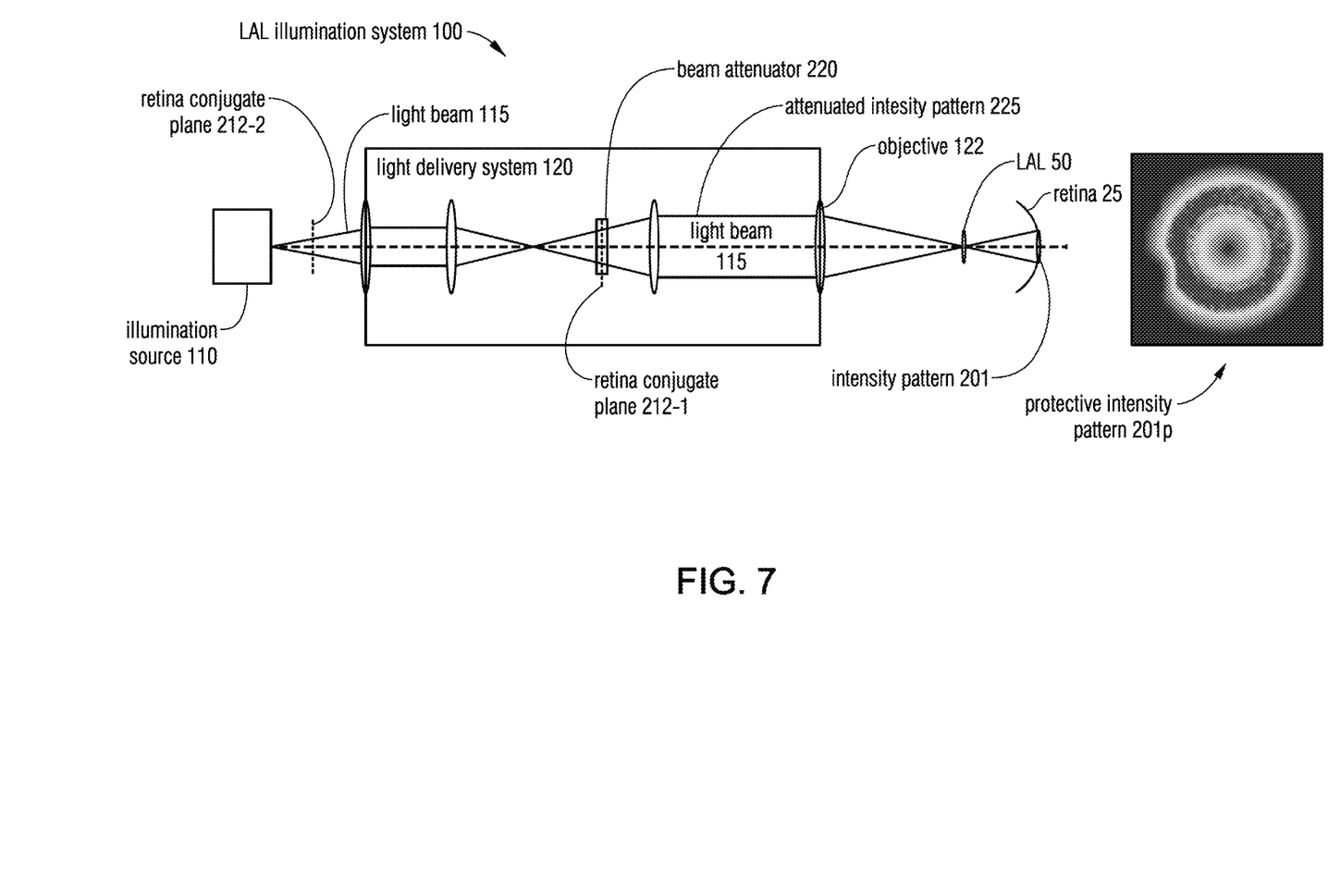
FIG. 7 illustrates a beam attenuator embodiment of the protective beam shaper.
Figure 8:
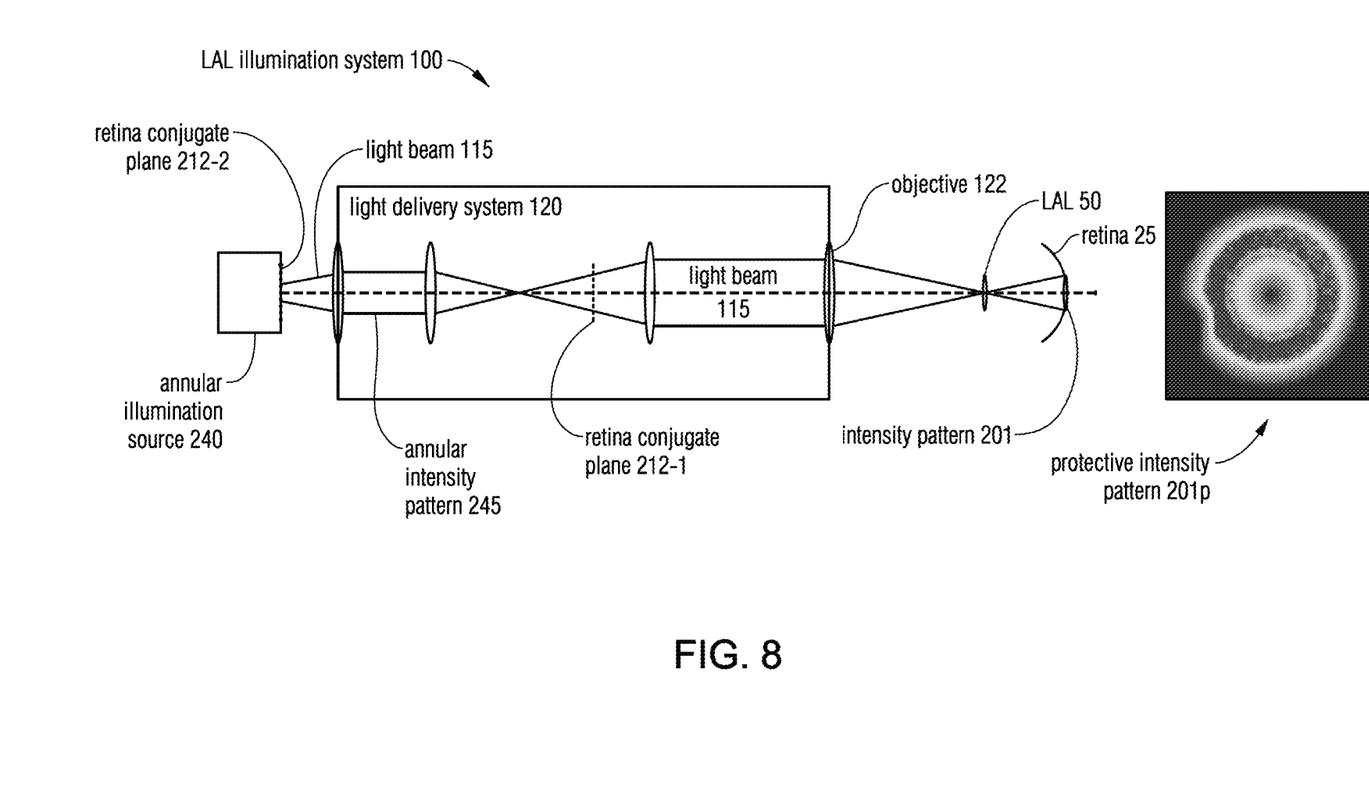
FIG. 8 illustrates an annular illumination source embodiment of the protective beam shaper.

FIGS. 6-8 illustrate various specific embodiments 210-240 of the protective beam-shaper 200. In general terms, these protective beam-shaper 200 embodiments can shape the light beam 115 by blocking, absorption, attenuated transmission, modulation, or reflection. In yet other embodiments, they can shape the generation of the light beam 115 itself.

FIG. 6 shows an embodiment where the protective beam-shaper 200 is part of the light delivery system 120 and includes a beam-stopping obscuration disk 210. This obscuration disk 210 can be positioned at an optical conjugate plane of the retina 25 of the eye 1, or retina conjugate plane 212-1 for short. The obscuration disk 210 can be precisely at this retina conjugate plane 212-1, or can be close to it, within a reasonable tolerance. Referencing well-known optical considerations of conjugate planes, the light delivery system 120 images the obscuration disk 210 positioned at the retina conjugate plane 212-1 sharply onto the retina 25. Objects positioned away from the retina conjugate plane 212-1 are not imaged sharply onto the retina 25, instead, they only form a blurry pattern on the retina 25.

Embodiments of the LAL illumination system 100 can include a beam modulator to modulate an intensity of the light beam 115 to create the earlier described adjustment intensity pattern. The beam modulator (not shown) can be positioned at a LAL conjugate plane 214-1. In some embodiments, the beam modulator 230 can include a digital mirror device with an actuatable micro-mirror-array, to receive the light beam 115 generated by the illumination source 110, and to reflect the received light beam 115 according to the adjustment intensity pattern. In some cases, this digital mirror device can redirect the light beam 115. The field of digital mirror devices is mature, and many solutions have been developed and are used, for example, in projectors and presenting devices. Any of these digital mirror devices can be used as the beam modulator, as well as non-mirror-based beam modulators.

The obscuration disk 210 is configured to stop a central portion of the light beam 115, thereby generating a centrally obscured intensity pattern 215, such that the relative central intensity reduction at the retina 25, Δ(ret), is greater than the relative central intensity reduction at the LAL plane, Δ(LAL). The far-right panel of FIG. 6 shows that the obscuration disk 210 stopping a central portion of the light beam 115 at the retina conjugate plane 212-1 that images sharply onto the retina 25 creates an intensity pattern 201 on the retina 25 that is a protective intensity pattern 201 in that the intensity in its central region 202 is reduced to essentially zero, making C(ret)≈0 and Δ(ret)≈1.

As shown in FIG. 6, there can be more than one retina conjugate planes, such as retina conjugate plane 212-2, depending on the complexity of the light delivery system 120. The obscuration disk 210 can be positioned into any of these retina conjugate planes 212-1 or 212-2. For orientation, the LAL conjugate plane 214-1 is also shown. Objects positioned at this LAL conjugate plane 214-1 are imaged onto the LAL plane. Various embodiments of the light delivery system 120 can have a wide variety of optical solutions, beyond the shown simple pairs of collimating lenses proximal and distal to the obscuration disk 210, and a distal focusing objective 122. Also, the obscuration disk 210 can be part of a beam aperture. Finally, the obscuration disk 210 can be more than a simple hard beam stop. For example, it can have an annulus whose transparency is increasing with increasing radius.

FIG. 7 illustrates another embodiment, where the protective beam-shaper 200 is again part of the light delivery system 120, but now operates in a transmission mode, and includes a beam-attenuator 220, to transmit the light beam 115 with an attenuated intensity pattern 225, such that the relative central intensity reduction at the retina 25, Δ(ret), is greater than the relative central intensity reduction at the LAL plane, Δ(LAL). As before, this beam attenuator 220 can be positioned at the retina conjugate plane 212-1. The beam attenuator 220 can include an LCD array that is operated in a transmission mode. The beam attenuator 220 can induce an attenuated intensity pattern 225 by gradually changing the transmission coefficient of the LCD array. As such, the intensity pattern 201 at the retina 25 can again be a protective intensity pattern 201p, while the variation of the intensity can be more gradual, as shown in the right panel of FIG. 7.

FIG. 8 illustrates that in some embodiments, the protective beam-shaper 200 and the illumination source 110 can be integrated into an annular illumination source 240, configured to generate the light beam 115 with an annular intensity pattern 245, such that the relative central intensity reduction at the retina 25, Δ(ret), is greater than the relative central intensity reduction at the LAL plane, Δ(LAL). The annular illumination source 240 can be positioned at the retina conjugate plane 212-2, and can generate a protective intensity pattern 201p on the retina 25.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A light adjustable lens illumination system, comprising:
an illumination source, for generating a light beam;
a light delivery system, for projecting the light beam onto a Light Adjustable Lens (LAL), implanted into an eye, so that a fraction of the light beam propagates past the LAL to a retina of the eye; and
a protective beam-shaper, for shaping the light beam to have an intensity pattern with a relative central intensity reduction that varies along an axis; wherein
the relative central intensity reduction at the retina is greater than the relative central intensity reduction at a LAL plane.

2. The LAL illumination system of claim 1, wherein:
the relative central intensity reduction of the intensity pattern of the light beam is a ratio of a maximum intensity minus a reduced beam center intensity, divided by the maximum intensity.

3. The LAL illumination system of claim 2, wherein:
a central region of the illumination pattern at the retina with the reduced beam center intensity is positioned to include a fovea of the eye.

4. The LAL illumination system of claim 3, wherein:
a diameter of the central region is less than 2 mm.

5. The LAL illumination system of claim 2, wherein:
the intensity pattern of the light beam at the retina is a protective intensity pattern in that the reduced beam center intensity in a central region is less than 0.1 $mW/cm^2$.

6. The LAL illumination system of claim 1, wherein:
the relative central intensity reduction at the retina is greater than 30%; and
the relative central intensity reduction at the LAL plane is less than 30%.

7. The LAL illumination system of claim 1, wherein:
the relative central intensity reduction at the retina is greater than 50%; and
the relative central intensity reduction at the LAL plane is less than 20%.

8. The LAL illumination system of claim 1, wherein:
a wavelength of the light beam is in a range of 300 nm-450 nm.

9. The LAL illumination system of claim 1, wherein:
the generated light beam is a lock-in beam, for locking in a previous light adjustment of the LAL.

10. The LAL illumination system of claim 1, wherein:
the protective beam-shaper is part of the light delivery system, and includes
a beam-stopping obscuration disk,
positioned at an optical conjugate plane of the retina of the eye within a tolerance,
to stop a central portion of the light beam, thereby generating a centrally obscured intensity pattern, such that the relative central intensity reduction at the retina is greater than the relative central intensity reduction at the LAL plane.

11. The LAL illumination system of claim 10, wherein:
the obscuration disk is part of a beam aperture.

12. The LAL illumination system of claim 1, wherein:
the protective beam-shaper is part of the light delivery system, and includes
a beam-attenuator, to transmit the light beam with an attenuated intensity pattern, such that the relative central intensity reduction at the retina is greater than the relative central intensity reduction at the LAL plane.

13. The LAL illumination system of claim 12, the beam-attenuator comprising:
an LCD array, operated in a transmission mode.

14. The LAL illumination system of claim 1, wherein:
the protective beam-shaper and the illumination source are integrated into an annular illumination source, configured to generate the light beam with an annular intensity pattern, such that the relative central intensity reduction at the retina is greater than the relative central intensity reduction at the LAL plane.

\* \* \* \* \*